(12) United States Patent
Kimura et al.

(10) Patent No.: US 10,572,730 B2
(45) Date of Patent: Feb. 25, 2020

(54) VISUAL LINE MEASURING DEVICE AND VISUAL LINE MEASURING METHOD

(71) Applicant: Panasonic Intellectual Property Management Co., Ltd., Osaka (JP)

(72) Inventors: Soichi Kimura, Osaka (JP); Hidetoshi Takeda, Osaka (JP); Shingo Yamazoe, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 78 days.

(21) Appl. No.: 15/814,558

(22) Filed: Nov. 16, 2017

(65) Prior Publication Data

US 2018/0089508 A1 Mar. 29, 2018

Related U.S. Application Data

(63) Continuation of application No. PCT/JP2017/005053, filed on Feb. 13, 2017.

(30) Foreign Application Priority Data

Apr. 13, 2016 (JP) .................................. 2016-080183

(51) Int. Cl.
*G06K 9/00* (2006.01)

(52) U.S. Cl.
CPC ....... *G06K 9/00604* (2013.01); *G06K 9/0061* (2013.01); *G06K 9/00255* (2013.01)

(58) Field of Classification Search
CPC ........... G06K 9/00604; G06K 9/00255; G06K 9/0061; G06F 3/0304; G06F 3/013; B60R 11/04; B60R 11/02; A61B 3/113
See application file for complete search history.

(56) References Cited

U.S. PATENT DOCUMENTS

2013/0188834 A1 7/2013 Ebisawa
2015/0277599 A1* 10/2015 Cho ...................... G06F 3/0418
345/173

FOREIGN PATENT DOCUMENTS

WO 2012/020760 2/2012

OTHER PUBLICATIONS

International Search Report of PCT application No. PCT/JP2017/005053 dated Mar. 28, 2017.
(Continued)

*Primary Examiner* — Joseph W Becker
(74) *Attorney, Agent, or Firm* — Greenblum & Bernstein, P.L.C.

(57) ABSTRACT

A visual line measuring device of the present disclosure includes a light source that emits light for forming a corneal reflection point on an eyeball of an object person who gazes at a predetermined gaze point, an image-capturing part that captures a plurality of facial images each of which includes the eyeball of the object person by which the light from the light source is reflected, a detector that calculates visual line information for each of the facial images captured by the image-capturing part, a calculation part that calculates correction information by using at least two sets of the visual line information being in a predetermined positional relation among a plurality of sets of the visual line information calculated by the detector, and a correction part that corrects the visual line information calculated by the detector, by using the correction information.

7 Claims, 5 Drawing Sheets

(56) References Cited

OTHER PUBLICATIONS

Takehiko Ohno et al., "Just Look at Two Points: A Gaze Tracking System with Easy Calibration", Journal of Information Processing Society of Japan, Apr. 2003, vol. 44, No. 4, pp. 1136-1149.

* cited by examiner

VISUAL LINE MEASURING DEVICE AND VISUAL LINE MEASURING METHOD

TECHNICAL FIELD

The present invention relates to a visual line measuring device and a visual line measuring method for correcting an individual variation of a visual line of an object person detected based on an eyeball image of the object person.

BACKGROUND ART

As a technique capable of measuring a visual line with high accuracy in a non-contact manner, a corneal reflection method has been known.

This method uses reflected light on an eyeball, and therefore the accuracy is largely affected by an individual variation of an eyeball shape. Accordingly, a measured visual line is corrected by using an error belonging to a person.

PTL 1 discloses a gaze point detection device including a plurality of stereo cameras for obtaining facial images of an object person, a light source disposed outside an opening of each of the stereo cameras, a control circuit, and an image processing device.

The image processing device calculates an angle of a visual line of the object person by using a function based on the facial images, calculates a direction of the visual line while correcting the function such that directions of visual lines calculated corresponding to the plurality of stereo cameras are close to each other, and detects a gaze point of the object person on a display screen.

CITATION LIST

Patent Literature

PTL 1: WO 2012-020760 A1

SUMMARY OF THE INVENTION

The present disclosure provides a visual line measuring device capable of detecting a visual line with high accuracy and also reducing a burden on a user.

The visual line measuring device of the present disclosure includes a light source, an image-capturing part, a detector, a calculation part, and a correction part.

The light source emits light for forming a corneal reflection point on an eyeball of an object person who gazes at a predetermined gaze point.

The image-capturing part captures a plurality of facial images each of which includes the eyeball of the object person by which the light from the light source is reflected.

The detector calculates visual line information for each of the facial images captured by the image-capturing part.

The calculation part calculates correction information by using at least two sets of the visual line information that are in a predetermined positional relation among a plurality of sets of the visual line information calculated by the detector.

The correction part corrects the visual line information calculated by the detector by using the correction information.

In a visual line measuring method of the present disclosure, a plurality of facial images is captured. The facial images each include an eyeball of an object person by which light from a light source emitting the light for forming a corneal reflection point on the eyeball of the object person who gazes at a predetermined gaze point is reflected.

Furthermore, in the visual line measuring method, visual line information for each of the facial images captured at an image-capturing step is calculated.

Furthermore, in the visual line measuring method, correction information is calculated by using at least two sets of the visual line information that are in a predetermined positional relation among a plurality of calculated sets of the visual line information.

Furthermore, the visual line measuring method includes a correction step of correcting the calculated visual line information by using the correction information.

The visual line measuring device of the present disclosure makes it possible to reduce a burden on a user and to detect a visual line with high accuracy.

DESCRIPTION OF EMBODIMENTS

Exemplary embodiments will now be described herein in detail with reference to the drawings appropriately.

However, a detailed description more than necessary may be omitted.

For example, a detailed description of an already known item and a duplicated description of a substantially identical configuration may be omitted.

Such omissions are aimed to prevent the following description from being redundant more than necessary, and to help those skilled in the art easily understand the following description.

Note that the attached drawings and the following description are provided for those skilled in the art to fully understand the present disclosure, and are not intended to limit the subject matter as described in the appended claims.

First Exemplary Embodiment

1. Configuration

[1-1. System Configuration]

Figure 1:
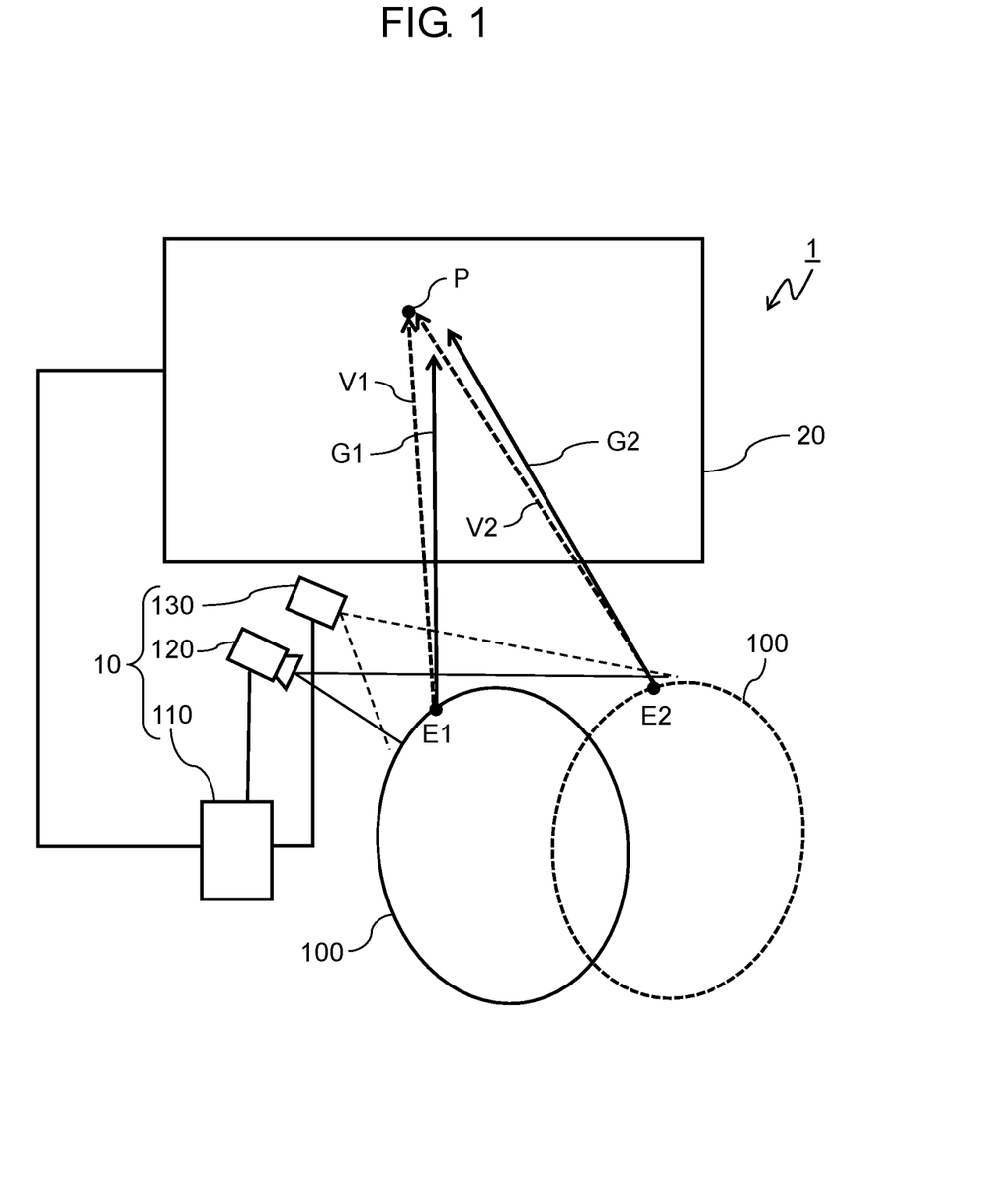
FIG. 1 illustrates a configuration example of a visual line measuring system according to a first exemplary embodiment.

FIG. 1 illustrates a configuration example of a visual line measuring system according to a first exemplary embodiment.

In FIG. 1, visual line measuring system 1 includes visual line measuring device 10 that measures a visual line of object person 100 and display 20 that displays a gaze destination for object person 100.

Further, visual line measuring device 10 includes image-capturing part 120 that captures facial images (eyeball images) of object person 100, light source 130 that emits light on an eyeball (not illustrated) of object person 100, and computing device 110 that performs visual line measurement of object person 100.

Display 20 displays gaze point P that is used as a gaze destination of object person 100.

Display 20 is only enough to be able to display the gaze destination of object person 100.

Display 20 is a display that includes a display element such as a liquid crystal display (LCD) panel or an organic electroluminescence (EL) display panel and a drive circuit that drives the display element.

Display 20 displays gaze point P according to control from visual line measuring device 10 or a controller (not illustrated).

Light source 130 is disposed at a predetermined position and emits light for forming the corneal reflection point on the eyeball of object person 100. Light source 130 is a light source that emits infrared light, for example.

Image-capturing part 120 captures the facial images of object person 100 that reflects the light emitted from light source 130.

Image-capturing part 120 is, for example, an infrared camera and captures the facial images of object person 100 by receiving the reflected light in which the infrared light emitted from light source 130 is reflected.

Before actual visual line measurement, computing device 110 detects visual line vectors (calculative visual line vectors G1, G2) of object person 100 from the facial images of object person 100 that are captured by image-capturing part 120.

Then, computing device 110 calculates correction information for correcting an individual variation, from a correspondence relation between real visual line vectors V1, V2 obtained from eyeball positions E1, E2 (pupil centers) of object person 100 and gaze point P, and calculative visual line vectors G1, G2.

Computing device 110 corrects detected calculative visual line vectors G1, G2, by using the calculated correction information.

[1-2. Configuration of Computing Device]

Figure 2:
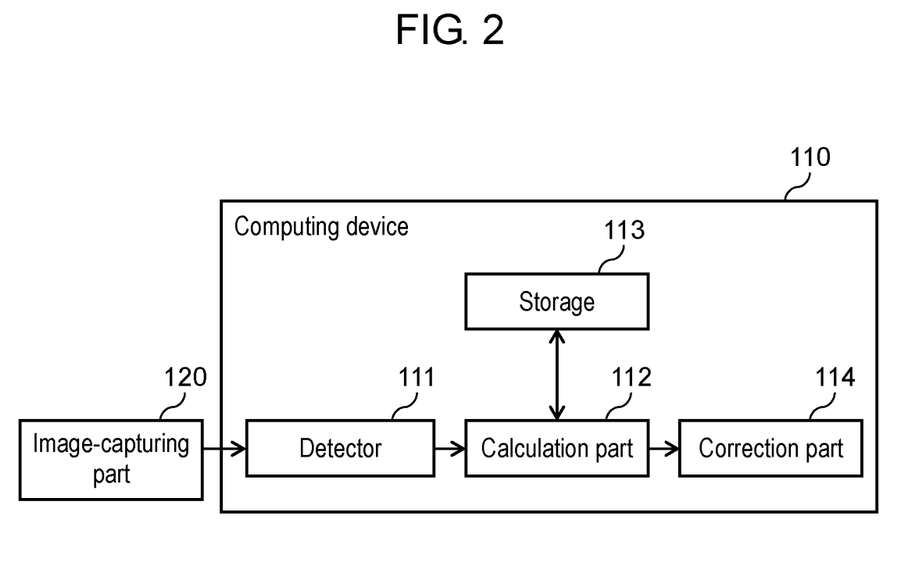
FIG. 2 is a block diagram illustrating a configuration example of a computing device according to the first exemplary embodiment.

FIG. 2 is a block diagram illustrating a configuration example of computing device 110.

In FIG. 2, computing device 110 includes detector 111, calculation part 112, storage 113, and correction part 114.

Functions of those functional parts are implemented by causing a central processing unit (CPU) to perform a program stored in a storage device such as a read-only memory (ROM), a magnetic disk, or an optical disk.

Detector 111 calculates calculative visual line vectors G1, G2 of object person 100 by using the facial images captured by image-capturing part 120.

Further, detector 111 calculates real visual line vectors V1, V2 from a positional relation between eyeball positions E1, E2 of object person 100 and gaze point P.

Detector 111 sends the calculated visual line vectors (calculative visual line vectors and real visual line vectors), eyeball positions E1, E2 of object person 100, and identification information (hereinafter, referred to as ID) that can uniquely identify object person 100, to calculation part 112 as visual line information.

Calculation part 112 stores the visual line information sent from detector 111 into storage 113.

Calculation part 112 selects at least two sets of the visual line information that are in a predetermined positional relation among a plurality of sets of the visual line information stored in storage 113, and calculates correction information for correcting a detection error caused by the individual variation of the eyeball.

Calculation part 112 outputs the visual line information and the correction information to correction part 114.

Storage 113 stores the visual line information and the correction information.

Storage 113 may be configured with a semiconductor memory or the like, and may be configured with a volatile memory, non-volatile memory, or the like.

Correction part 114 corrects the visual line information calculated by detector 111 by using the correction information calculated by calculation part 112.

[1-3. Error Caused by Individual Variation of Eyeball]

Figure 3:
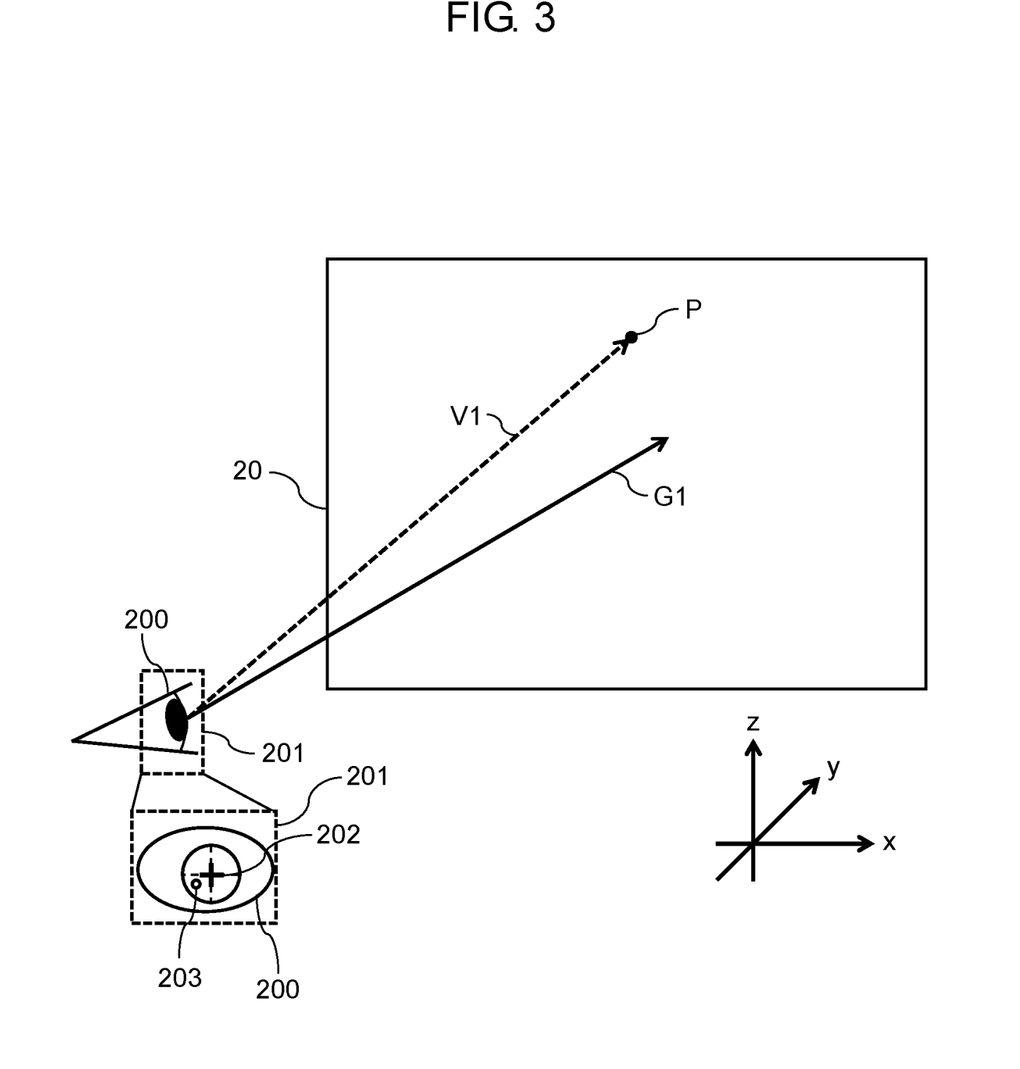
FIG. 3 is a diagram describing visual line information.

FIG. 3 is a diagram describing the visual line information.

In FIG. 3, it is assumed that, with respect to object person 100, a horizontal direction is an x-axis, a vertical direction is a z-axis, and a front-back direction is a y-axis, starting from pupil center 202.

FIG. 3 illustrates a state in which gaze point P whose position is known is displayed on display 20, and object person 100 gazes at gaze point P.

Here, as illustrated in FIG. 3, a visual line of object person 100 is defined by a visual line vector (real visual line vector V1) extending from pupil center 202 toward gaze point P on display 20, in pupil region 201 present in eyeball 200 of object person 100.

Calculative visual line vector G1 of object person 100 calculated by detector 111 by using a visual line detection method represented by a corneal reflection method and the like is a vector including an error associated with the individual variation of object person 100.

As illustrated in FIG. 3, calculative visual line vector G1 is different from real visual line vector V1.

Pupil center 202 is obtained by detecting pupil region 201 by using a calculation method such as clustering or elliptic approximation, and obtaining center coordinates of pupil region 201.

As illustrated in FIG. 3, Purkinje image 203 (corneal reflection point) that is the reflected light of the light emitted from light source 130 is present on eyeball 200 of object person 100.

Here, the individual variation of person 100 is caused by variations in a light refractive index at a corneal surface of eyeball 200 of object person 100 as illustrated in FIG. 3, refraction caused by eye glasses and the like, an eyeball shape, a shift between an eyeball center and a fovea centralis, and the like, for each person.

In a correction process described later, a detection error caused by those variations is reduced by using correction information unique to each person.

[1-4. Correction Information]

In the present disclosure, the corneal reflection method will be described as the visual line detection method.

The corneal reflection method is for calculating a visual line from a positional relation between a pupil position and Purkinje image.

With the corneal reflection method, before visual line measurement, correction information is calculated based on a correspondence relation between a visual line vector calculated from a facial image capturing an object person who gazes at a known point, and an actual visual line vector.

The corneal reflection method is for correcting a visual line vector calculated during the visual line measurement by using correction information (correction values) including a coefficient and a constant term (an adding value) for an angle, by using the following equation (Equation 1).

$$A = \begin{pmatrix} rA \\ \theta A \\ \phi A \\ 1 \end{pmatrix} = HB = \begin{pmatrix} 1 & 0 & 0 & 0 \\ 0 & \omega 1 & 0 & \omega 2 \\ 0 & 0 & \omega 3 & \omega 4 \\ 0 & 0 & 0 & 1 \end{pmatrix} \begin{pmatrix} rB \\ \theta B \\ \phi B \\ 1 \end{pmatrix} = \begin{pmatrix} rB \\ \omega 1 \theta B + \omega 2 \\ \omega 3 \phi B + \omega 4 \\ 1 \end{pmatrix}$$ (Equation 1)

In the corneal reflection method, when elevation angle θB and azimuth angle φB of visual line vector before correction B are respectively corrected to elevation angle θA and azimuth angle φA of visual line vector after correction A, correction information for angles of a visual line vector is defined as matrix H in the equation (Equation 1).

In this case, in order to obtain the correction information, information obtained when object person 100 gazes at a gaze point from a plurality of positions is required.

The present disclosure uses information obtained when object person 100 gazes at gaze point P from two different positions, in order to obtain the correction information.

2. Operation

Here, as illustrated in FIG. 1, a case where display 20 displays gaze point P, and object person 100 is made to gaze at gaze point P during a predetermined period is described as an example.

It is noted that, object person 100 may move his or her head, as long as object person 100 gazes at gaze point P during the predetermined period.

2-1. Whole Operation

Figure 4:
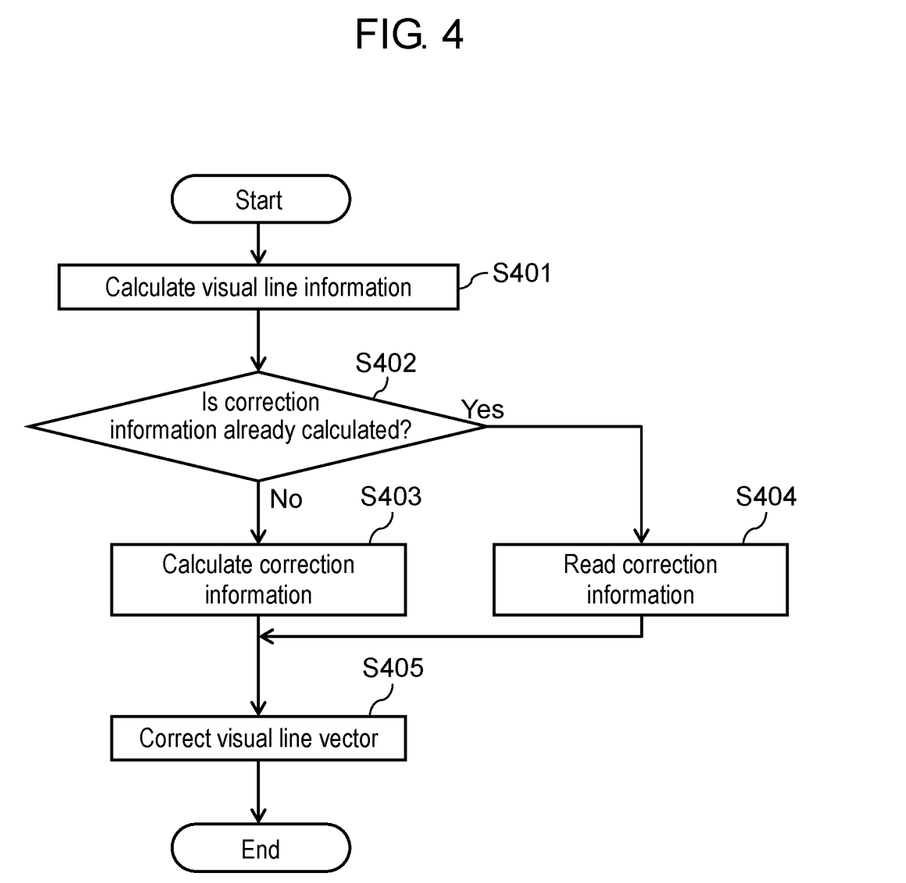
FIG. 4 is a flow chart for describing an operation of a visual line measuring device according to the first exemplary embodiment.

FIG. 4 is a flow chart for explaining an operation of visual line measuring device 10 according to the first exemplary embodiment.

Detector 111 performs a visual-line detection process for calculating a calculative visual line vector of object person 100, by using facial images captured by image-capturing part 120 when object person 100 gazes at gaze point P (step S401).

Further, detector 111 calculates a real visual line vector from a positional relation between pupil center 202 of object person 100 and gaze point P.

Detector 111 associates a pair of the calculative visual line vector and the real visual line vector with ID uniquely indicating object person 100 to send the resultant information to calculation part 112 as visual line information.

Calculation part 112 stores the received visual line information into storage 113 (step S402).

Storage 113 examines, by using the ID, whether correction information associated with object person 100 is already calculated.

As a result, when the correction information for object person 100 is present, that is, when the correction information for object person 100 is already calculated (Yes in step S402), the process proceeds to step S404, and when the correction information for object person 100 is not calculated (No in step S402), the process proceeds to step S403.

Calculation part 112 performs a correction information calculating process for calculating correction information for an individual variation of a visual line, by using at least two sets of the visual line information that are in a predetermined positional relation among a plurality of sets of the visual line information stored in storage 113 (step S403).

Calculation part 112 stores the calculated correction information associating with the ID into storage 113.

Calculation part 112 sends the visual line information and the calculated correction information to correction part 114.

It is noted that, when at least two sets of visual line information each of which includes a different pair of the real visual line vector and the calculative visual line vector are not stored in storage 113, calculation part 112 dose not calculate the correction information, and sends average correction values as the correction information to correction part 114, together with the visual line information.

Calculation part 112 reads the correction information associated with the received ID, from storage 113, and sends the correction information to correction part 114, together with the visual line information (step S404).

Correction part 114 performs the correction process for correcting the calculative visual line vector using the equation (Equation 1), based on the visual line information and the correction information sent from calculation part 112, and calculates a visual line vector after correction (corrected visual line vector) (step S405).

Hereinafter, each process will be described in detail.

2-2. Visual-Line Detection Process

With reference to FIG. 3, a case where gaze point P is displayed on display 20 is described as an example.

Image-capturing part 120 captures a facial image of object person 100 who gazes at gaze point P on display 20, and sends the image data to detector 111.

It is noted that, an image-capturing timing can be arbitrarily set, and may be controlled by a signal sent from an external device separately disposed, for example.

Detector 111 obtains an eyeball image in which a portion near an eyeball of object person 100 is segmented from the facial image captured by image-capturing part 120.

Here, image-capturing part 120 may capture the facial image of object person 100, so that the facial image includes only one eye, or includes both eyes.

Further, detector 111 may obtain, as the eyeball image of object person 100, an eyeball image of only one eye, or an eyeball image of each of both eyes.

The eye of object person 100 is an eyeball surface including an iris, a white of the eye, and an eyelid.

Next, as illustrated in FIG. 3, detector 111 calculates calculative visual line vector G1 by using a positional relation between pupil center 202 of object person 100, Purkinje image 203, image-capturing part 120, and light source 130, through the corneal reflection method.

Here, it is assumed that three-dimensional positions of image-capturing part 120 and light source 130 that are required to calculate calculative visual line vector G1 are obtained as known points, and are stored in a storage (not illustrated) in visual line measuring device 10 in advance.

Further, three-dimensional positions of pupil center 202 of object person 100 and Purkinje image 203 may be obtained by using a stereo camera, or by using a distance measuring method other than the stereo camera.

The three-dimensional positions of pupil center 202 of object person 100 and Purkinje image 203 are also stored in storage 113 described above.

Specifically, detector 111 segments pupil region 201 from the facial image of object person 100 captured by image-capturing part 120 when object person 100 gazes at gaze point P on display 20.

Detector 111 calculates calculative visual line vector G1 of object person 100 based on the positions of image-capturing part 120 and light source 130 and the positions of pupil center 202 and Purkinje image 203.

Further, detector 111 calculates real visual line vector V1 from a positional relation between pupil center 202 and gaze point P in three dimensions, of object person 100.

Detector 111 performs the above-mentioned processes on each facial image output from image-capturing part 120.

Detector 111 sends, for each facial image, positional information of object person 100, the ID of object person 100, pupil center 202, the pair of the calculative visual line vector and the real visual line vector, as the visual line information.

2-3. Correction Information Calculating Process

Calculation part 112 selects two sets of the visual line information each of which has a different position of pupil center 202 from each other among the plurality of sets of the visual line information stored in storage 113.

Here, as illustrated in FIG. 1, pupil centers 202 in two sets of the visual line information are described as eyeball positions E1, E2.

Calculation part 112 statistically calculates the correction information for the individual variation of the visual line, by using respective pairs of real visual line vectors V1, V2 obtained when one gaze point P is gazed from different eyeball positions E1, E2 and calculative visual line vectors G1, G2.

Here, depending on eyeball positions E1, E2 of object person 100, accurate correction information may not be calculated.

Specifically, when both differences in the elevation angle and the azimuth angle between the two calculated real visual line vectors and both differences in the elevation angle and the azimuth angle between the two calculative visual line vectors are less than a certain value, the correction information cannot be calculated.

This is because the correction information is calculated using differences in the angles obtained when one point is gazed from different eyeball positions.

Figure 5:
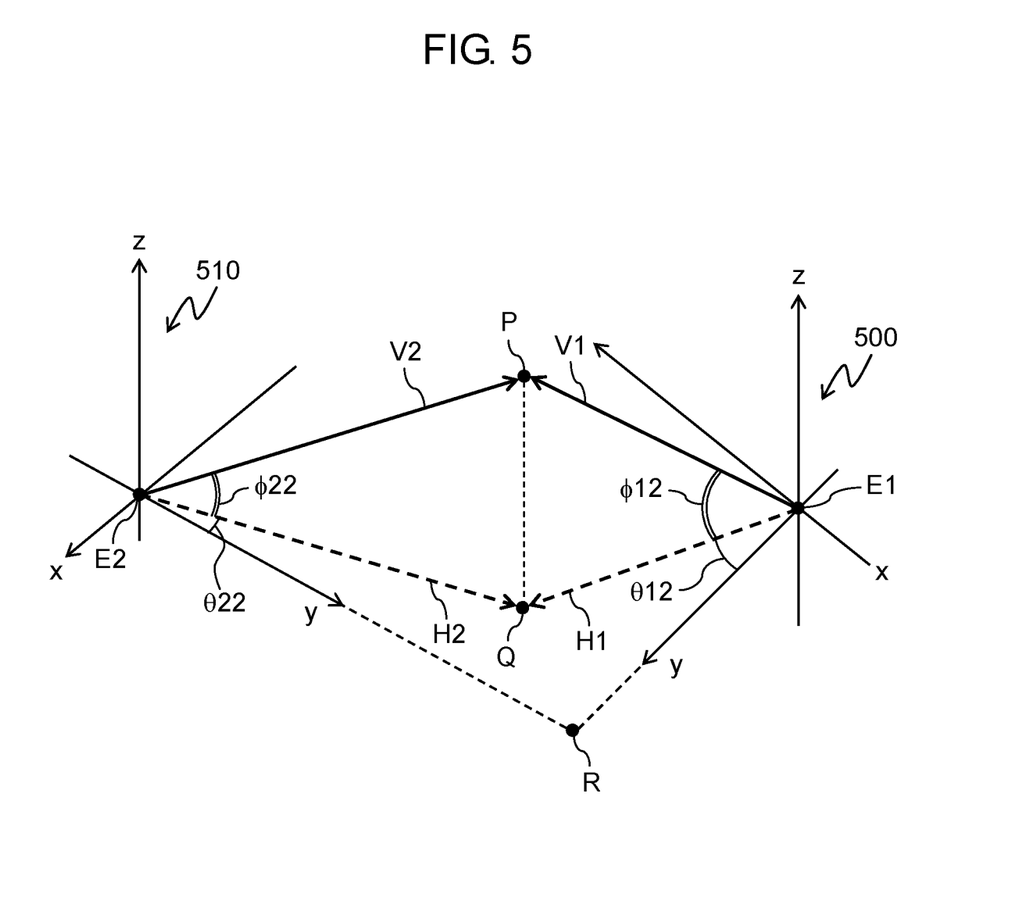
FIG. 5 is a diagram describing a positional relation between two selected sets of the visual line information, according to the first exemplary embodiment.

FIG. 5 is a diagram describing a positional relation between two selected sets of the visual line information.

As illustrated in FIG. 5, in the present exemplary embodiment, an orthogonal coordinate system is set for each eyeball position, and elevation angles and azimuth angles of the calculated real visual line vector and the calculative visual line vector are calculated.

In FIG. 5, point R indicates an arbitrary point present in front of object person 100.

Coordinate system 500 is a coordinate system in which a straight line passing through point R and eyeball position E1 is set as a y-axis that is one of reference axes of the orthogonal coordinate system.

Coordinate system 510 is a coordinate system in which a straight line passing through point R and eyeball position E2 is set as a y-axis that is one of reference axes of the orthogonal coordinate system. That is, eyeball positions E1, E2 and point R are located on the same plane (x-y plane). Point Q is a point in which gaze point P is projected on the x-y plane.

Vector H1 is a vector in which calculative visual line vector G1 is projected on the x-y plane, in coordinate system 500.

Similarly, vector H2 is a vector in which calculative visual line vector G2 is projected on the x-y plane, in coordinate system 510. Further, deflection angle θ12 is an angle formed by vector H1 and calculative visual line vector G1 (the elevation angle). Deflection angle φ12 indicates an angle formed by vector H1 and the y-axis (azimuth angle). Similarly, deflection angle θ22 is an angle formed by vector H2 and calculative visual line vector G2 (the elevation angle). Deflection angle φ22 indicates an angle formed by vector H2 and the y-axis (the azimuth angle).

As illustrated in FIG. 5, when gaze point P is viewed from different eyeball positions E1, E2 by moving the head, the elevation angle and the azimuth angle of each of real visual line vectors V1, V2 change according to eyeball positions E1, E2.

It is noted, in FIG. 5, a description is given using real visual line vectors V1, V2, but deflection angles θ11, φ11 of calculative visual line vector G1 and deflection angles θ21, φ21 of calculative visual line vector G2 change in the same manner.

In the present exemplary embodiment, among sets of the visual line information obtained when identical gaze point P is gazed from different eyeball positions E1, E2, calculation part 112 selects two sets of the visual line information in which both differences in the elevation angle and the azimuth angle between real visual line vectors V1, V2 are equal to or more than a predetermined angle.

Calculation part 112 calculates the correction information based on an angular relation between real visual line vectors V1, V2 of the selected sets of the visual line information and calculative visual line vector G1, G2.

2-4. Specific Example

Hereinafter, a case where display 20 displays gaze point P, and object person 100 is made to gaze at gaze point P during a predetermined period to measure a visual line of object person 100 is described with reference to FIG. 1, FIG. 2, and FIG. 5.

Here, it is assumed that object person 100 may move his or her head, as long as person 100 gazes at gaze point P.

In the present exemplary embodiment, image-capturing part 120 is assumed to capture two facial images A, B during the predetermined period.

First, visual line measuring device 10 causes display 20 to display gaze point P, and causes object person 100 to gaze at gaze point P during the predetermined period.

Image-capturing part 120 captures images of object person 100 gazing at gaze point P, and outputs facial images A, B to detector 111.

Detector 111 obtains the eyeball image from facial image A captured by image-capturing part 120, and calculates eyeball position E1 and calculative visual line vector G1 from the eyeball image.

Calculative visual line vector G1 is represented as a vector in a polar coordinate system as shown in the following equation (Equation 2).

$$G1 = \begin{pmatrix} r11 \\ \theta 11 \\ \phi 11 \\ 1 \end{pmatrix} \quad \text{(Equation 2)}$$

In the equation (Equation 2), diameter r11 is a diameter of the vector, and is a distance from eyeball position E1 to gaze point P on display 20.

Diameter r11 of the vector may be set to 1 as a unit vector.

Further, deflection angle θ11 is an elevation angle of calculative visual line vector G1 explained in FIG. 5, and deflection angle φ11 is an azimuth angle of calculative visual line vector G1.

Further, detector 111 calculates real visual line vector V1 based on a position of gaze point P on display 20 and eyeball position E1.

Real visual line vector V1 is represented as a vector in a polar coordinate system as shown in the following equation (Equation 3), similarly to calculative visual line vector G1.

$$V1 = \begin{pmatrix} r12 \\ \theta 12 \\ \phi 12 \\ 1 \end{pmatrix} \quad \text{(Equation 3)}$$

However, in the equation (Equation 3), diameter r12 is a diameter of the vector.

Diameter r12 of the vector may be set to 1 as a unit vector.

Further, deflection angle θ12 is an elevation angle of real visual line vector V1, and deflection angle φ12 is an azimuth angle of real visual line vector V2.

Detector 111 sends visual line information including eyeball position E1 and a pair of real visual line vector V1 and calculative visual line vector G1 calculated by using facial image A, and the ID of object person 100 to calculation part 112.

Next, detector 111 obtains the eyeball image from facial image B captured by image-capturing part 120, and calculates eyeball position E2 and calculative visual line vector G2 from the eyeball image.

Calculative visual line vector G2 is represented as a vector in a polar coordinate system as shown in the following equation (Equation 4).

$$G2 = \begin{pmatrix} r21 \\ \theta 21 \\ \phi 21 \\ 1 \end{pmatrix} \quad \text{(Equation 4)}$$

However, in the equation (Equation 4), diameter r21 is a diameter of the vector.

Diameter r21 of the vector may be set to 1 as a unit vector.

Further, deflection angle θ21 is an elevation angle of calculative visual line vector G2, and deflection angle φ21 is an azimuth angle of calculative visual line vector G2.

Detector 111 calculates real visual line vector V2 based on the position of gaze point P on display 20 and eyeball position E2.

Real visual line vector V2 is represented as a vector in a polar coordinate system as shown in the following equation (Equation 5), similarly to calculative visual line vector G2.

$$V2 = \begin{pmatrix} r22 \\ \theta 22 \\ \phi 22 \\ 1 \end{pmatrix} \quad \text{(Equation 5)}$$

However, in the equation (Equation 5), diameter r22 is a diameter of the vector.

Diameter r22 of the vector may be set to 1 as a unit vector.

Further, deflection angle θ22 is an elevation angle of real visual line vector V2, and deflection angle φ22 is an azimuth angle of real visual line vector V2.

Detector 111 sends visual line information including eyeball position E2 and a pair of real visual line vector V2 and calculative visual line vector G2 calculated by using facial image B, and the ID of object person 100 to calculation part 112.

Calculation part 112 examines, by using the ID of object person 100, whether the correction information of object person 100 is stored in storage 113.

When the correction information is stored in storage 113, calculation part 112 reads the correction information stored in storage 113, and sends the visual line information received from detector 111 and the correction information to correction part 114.

Further, when the correction information of object person 100 is not stored in storage 113, that is, when the correction information is not calculated, calculation part 112 calculates the correction information.

In this case, calculation part 112 records the visual line information sent from detector 111 into storage 113, and calculates correction information on the visual line for the person by using two sets of the visual line information recorded in storage 113. Storage 113 may also record a position of light source 130.

Calculation part 112 reads the visual line information recorded in storage 113 by using the ID, and performs the correction information calculating process.

In this case, calculation part 112 reads two sets of the visual line information calculated by using facial images A, B.

When visual line vectors calculated for two points are not included in the visual line information, calculation part 112 does not calculate the correction information.

In this case, calculation part 112 may send average correction values as the correction information to correction part 114.

Calculation part 112 calculates ω1, ω2, ω3, and ω4 in matrix H indicated in the equation (Equation 1), by using a pair of calculative visual line vector G1 and real visual line vector V1, and a pair of calculative visual line vector G2 and real visual line vector V2.

For example, calculation part 112 calculates matrix H that is the correction information, by substituting real visual line vector V1 into visual line vector after correction A, and substituting calculative visual line vector G1 into visual line vector before correction B.

For this calculation method, a least squares method in which an error between the calculative visual line vector and the real visual line vector is minimized may be used.

After calculating matrix H, calculation part 112 outputs the visual line information and the calculated correction information.

Correction part 114 corrects the calculative visual line vector by using the visual line information, the correction information, and the equation (Equation 1), and calculates the corrected visual line vector. Correction part 114 outputs the corrected visual line vector.

3. Advantageous Effects Etc

In visual line measuring device 10 of the present disclosure, light source 130 emits light for forming a corneal reflection point on an eyeball of object person 100 who gazes at a predetermined gaze point, and image-capturing part 120 captures a plurality of facial images of object person 100, by which the light from light source 130 is reflected.

Detector 111 calculates visual line information for each of the facial images captured by image-capturing part 120.

Calculation part 112 calculates correction information by using at least two sets of the visual line information that are in a predetermined positional relation among a plurality of sets of the visual line information calculated by detector 111.

Correction part 114 corrects the visual line information calculated by detector 111 by using the correction information.

With this configuration, calculation part 112 can calculate the correction information of the visual line vector unique to each person from the visual line information measured in a state where object person 100 naturally moves his or her head.

Accordingly, a burden on object person 100 can be reduced, and a visual line can be detected with high accuracy.

It is noted that, in the present exemplary embodiment, a description is given assuming that gaze point P to be used for the calculation of the correction information is displayed on display 20, but gaze point P can be set on an object that is located in front of the object person and whose position is known.

For example, in a case of a vehicle cabin, a traffic signal located in front of the vehicle or a speed meter in the vehicle cabin can be used as gaze point P.

In this case, gaze point P is assumed to be set at a center of the object located in front of object person 100.

However, gaze point P may be set at a point at which object person 100 often gazes in the object, or, when a region of the object is clear, gaze point P may be set at, for example, an average position of the region.

In subsequent processes, similarly to a case where the calculation is performed by using gaze point P on display 20, a movement of the eyeball position of object person 100 is detected, and the calculation of the real visual line vectors, the calculative visual line vectors, and the correction values are performed.

OTHER EXEMPLARY EMBODIMENTS

As described above, the first exemplary embodiment has been described as illustration of the technique disclosed in this application.

However, the technique of the present disclosure is not limited to the first exemplary embodiment, but can be applied to exemplary embodiments where modifications, replacements, additions, omissions, and the like are appropriately made.

In addition, components described in the first exemplary embodiment can be combined to configure a new exemplary embodiment. Then, other exemplary embodiments will now be described herein.

In first exemplary embodiment, one light source is used, but a plurality of light sources may be used.

In first exemplary embodiment, the gaze point is displayed on display 20 in order to cause object person 100 to gaze at gaze point 10.

What is displayed on display 20 is not limited to the point, and, for example, contents may be displayed at a reference position to induce object person 100 to gaze at the contents.

In this case, the calculation may be performed by using the reference position in the contents as the gaze point.

It is noted that, the visual line information calculated by visual line measuring device 10 may be displayed on display 20.

In this case, an intersection between the calculative visual line vector and display 20 may be calculated, and may be output as gaze destination information.

In the present exemplary embodiment, calculation part 112 generates the correction information by using two sets of the visual line information, but calculation part 112 may select three or more sets of the visual line information, and may calculate the correction information by using all of those sets of the visual line information.

Further, final correction information may be generated based on a plurality of calculated sets of the correction information obtained by combining two sets of the visual line information.

For example, the plurality of calculated sets of the correction information obtained by combining two sets of the visual line information may be averaged. With this configuration, accuracy of the correction information can be improved.

INDUSTRIAL APPLICABILITY

The present disclosure is applicable to a visual line detection device for measuring a visual line in a non-contact manner.

Specifically, the present disclosure is applicable to behavior analysis of an object person such as monitoring of a driver in a vehicle cabin, an operation of an apparatus by using a visual line, or other applications.

REFERENCE MARKS IN THE DRAWINGS 1 visual line measuring system
10 visual line measuring device
20 display
110 computing device
111 detector
112 calculation part
113 storage
114 correction part
120 image-capturing part
130 light source
200 eyeball
201 pupil region
202 pupil center
203 Purkinje image
500, 510 coordinate system
G1, G2 calculative visual line vector
H matrix
P gaze point
V1, V2 real visual line vector

The invention claimed is:

1. A visual line measuring device, comprising: a light source that emits light for forming a corneal reflection point on an eyeball of an object person who gazes at a predetermined gaze point; a camera that captures at least two facial images each of which includes the eyeball of the object person by which the light emitted from the light source is reflected, the at least two images including a first image and a second image that differs from the first image, the first image including the eyeball of the object person at a first eyeball position, the second image including the eyeball of the object person at a second eyeball position that differs from the first eyeball position; a processor; and a memory including a set of instructions that, when executed by the processor, causes the processor to perform operations including: calculating visual line information based on the at least two images, the visual line information including at least first visual line information and second visual line information, the first visual line information being calculated based on the first image, the second visual line information being calculated based on the second image, the first visual line information including a first calculative visual line vector of the object person, the first calculative visual line vector including a first elevation angle and a first azimuth angle, the second visual line information including a second calculative visual line vector of the object person, the second calculative visual line vector including a second elevation angle and a second azimuth angle; selecting the first visual line information and the second visual line information among the visual line information; calculating correction information by using the first visual line information and the second visual line information; and correcting the first visual line information and the second visual line information, by using the correction information, wherein the correction information is calculated when a first difference and a second difference are both equal to or greater than a predetermined value, the first difference is between the first elevation angle of the first calculative visual line vector and the second elevation angle of the second calculative visual line vector, and the second difference is between the first azimuth angle of the first calculative visual line vector and the second azimuth angle of the second calculative visual line vector; wherein the calculating of the correction information includes: calculating a first real visual line vector of the object person based on the first eyeball position of the object person and the predetermined gaze point, the first real visual line vector including a third elevation angle and a third azimuth angle; calculating a second real visual hoe vector of the object person based on the second eyeball position of the object person and the predetermined gaze point, the second real visual line vector including a fourth elevation angle and a fourth azimuth angle; wherein the correction information corrects an individual variation of the object person, from a correspondence relation between the first real visual line vector and the second real visual line vector obtained from the first eyeball position and the second eyeball position of the object person and the predetermined gaze point, and the first calculative visual line vector and the second calculative visual line vector.

2. The visual line measuring device according to claim 1, wherein the predetermined gaze point is a point displayed on a display disposed in front of the object person, or a point on an object disposed in front of the object person.

3. The visual line measuring device according to claim 1, wherein the correction information includes a coefficient and an adding value for at least one of the angles of each of the first visual line vector and the second visual line vector.

4. The visual line measuring device according to claim 1, wherein
the first eyeball position and the second eyeball position are different relative to the predetermined gaze point.

5. The visual line measuring device according to claim 4, wherein
the first eyeball position and the second eyeball position are different relative to the camera, and
the first eyeball position and the second eyeball position are different relative to the light source.

6. The visual line measuring device according to claim 1, wherein
the predetermined gaze point includes a traffic signal located in front of a vehicle or a speed meter in a cabin of the vehicle.

7. A visual line measuring method, comprising: capturing at least two images each of which includes an eyeball of an object person, by which light from a light source emitting the light for forming a corneal reflection point on the eyeball of the object person who gazes at a predetermined gaze point is reflected, the at least two images including a first image and a second image that differs from the first image, the first image including the eyeball of the object person at a first eyeball position, the second image including the eyeball of the object person at a second eyeball position that differs from the first eyeball position; calculating visual line information based on the at least two images, the visual line information including at least first visual line information and second visual line information, the first visual line information being calculated based on the first image, the second visual line information being calculated based on the second image, the first visual line information including a first calculative visual line vector of the object person, the first calculative visual line vector including a first elevation angle and a first azimuth angle, the second visual line information including a second calculative visual line vector of the object person, the second calculative visual line vector including a second elevation angle and a second azimuth angle; selecting the first visual line information and the second visual line information among the visual line information; calculating correction information by using the first visual line information and the second visual line information; and correcting the first visual line information and the second visual line information, by using the correction information, wherein the correction information is calculated when a first difference and a second difference are both equal to or greater than a predetermined value; the first difference is between the first elevation angle of the first calculative visual line vector and the second elevation angle of the second calculative visual line vector, and the second difference is between the first azimuth angle of the first calculative visual line vector and the second azimuth angle of the second calculative visual line vector; wherein the calculating of the correction information includes: calculating a first real visual line vector of the object person based on the first eyeball position of the object person and the predetermined gaze point, the first real visual line vector including a third elevation angle and a third azimuth angle; calculating a second real visual line vector of the object person based on the second eyeball position of the object person and the predetermined gaze point, the second real visual line vector including a fourth elevation angle and a fourth azimuth wherein the correction information corrects an individual variation of the object person, from a correspondence relation between the first real visual line vector and the second real visual line vector obtained from the first eyeball position and the second eyeball position of the object person and the predetermined gaze point, and the first calculative visual line vector and the second calculative visual line vector.

* * * * *